United States Patent [19]

Botha et al.

[11] Patent Number: 5,395,302
[45] Date of Patent: Mar. 7, 1995

[54] PROTECTIVE SHEATH FOR AN INJURED LIMB

[75] Inventors: Rudolph P. Botha, Roodepoort; Rainer Hohendorf, Pretoria, both of South Africa

[73] Assignee: Limbtech (Proprietary) Limited, Transvaal, South Africa

[21] Appl. No.: 139,189

[22] Filed: Oct. 19, 1993

[30] Foreign Application Priority Data

Oct. 21, 1992 [ZA] South Africa ............ 92/8131

[51] Int. Cl.$^6$ ............................................. A61F 5/00
[52] U.S. Cl. .................................... 602/3; 128/849
[58] Field of Search ............... 602/3, 20, 23; 128/846, 128/849; 2/59, 60, 16, 126

[56] References Cited

U.S. PATENT DOCUMENTS

| 1,980,486 | 11/1934 | King et al. | |
|---|---|---|---|
| 2,244,871 | 6/1941 | Guinzburg | |
| 3,735,759 | 5/1973 | MacKay | |
| 3,741,203 | 6/1973 | Liman | 602/3 |
| 3,747,125 | 7/1973 | Goldman et al. | |
| 3,785,374 | 1/1974 | Lipson | |
| 3,906,941 | 9/1975 | Cook, Jr. | |
| 4,036,220 | 7/1977 | Bellasalma | |
| 4,043,326 | 8/1977 | Little et al. | |
| 4,254,765 | 3/1981 | Brown et al. | |
| 4,363,317 | 12/1982 | Broucek | 602/3 |
| 4,406,281 | 9/1983 | Hubbard et al. | |
| 4,523,586 | 6/1985 | Couri | 602/3 |
| 4,530,350 | 7/1985 | Brown et al. | 602/3 |
| 4,610,245 | 9/1986 | Biearman | 602/3 |
| 4,639,945 | 2/1987 | Betz | |
| 4,649,910 | 3/1987 | Poenitsch | |
| 4,727,864 | 3/1988 | Wiesenthal et al. | 602/3 |
| 4,911,151 | 3/1990 | Rankin et al. | 602/3 |

FOREIGN PATENT DOCUMENTS 910015 1/1991 South Africa .
2161364A 1/1986 United Kingdom .

OTHER PUBLICATIONS

"Patient Protectors, Smocks & Cast Protectors"–Duro-Med Industries, Inc. (Undated)–1 page.
"Orthopedic And Sports Medicine"–McKesson Home Heath Care (Undated)–1 page.

Primary Examiner—Linda C. M. Dvorak
Attorney, Agent, or Firm—Harness, Dickey & Pierce

[57] ABSTRACT

The limb sheath is used to provide a waterproof cover for an injured limb, such as a burned limb or a limb which is bandaged or in a cast. The sheath has a water impervious sleeve made of a first plastics material. The sleeve has an open end through which a limb can be inserted. A sealing strip is fastened to and extends about the internal surface of the sleeve at the open end. The sealing strip is made of a second plastics material which is more highly plasticised than the first plastics material. There is also an elastic strap which is connected to and extends from the sleeve adjacent the open end. The strap is fastenable to itself by mating components of a self-contact fastener. In use with the sealing strip in contact with the limb, the strap can be stretched resiliently, wrapped about the open end and fastened to itself, thereby pressing the sealing strip against the limb to form a water-tight seal at the open end.

6 Claims, 2 Drawing Sheets

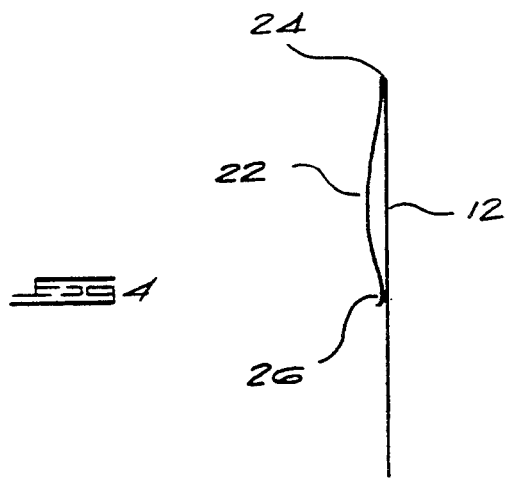
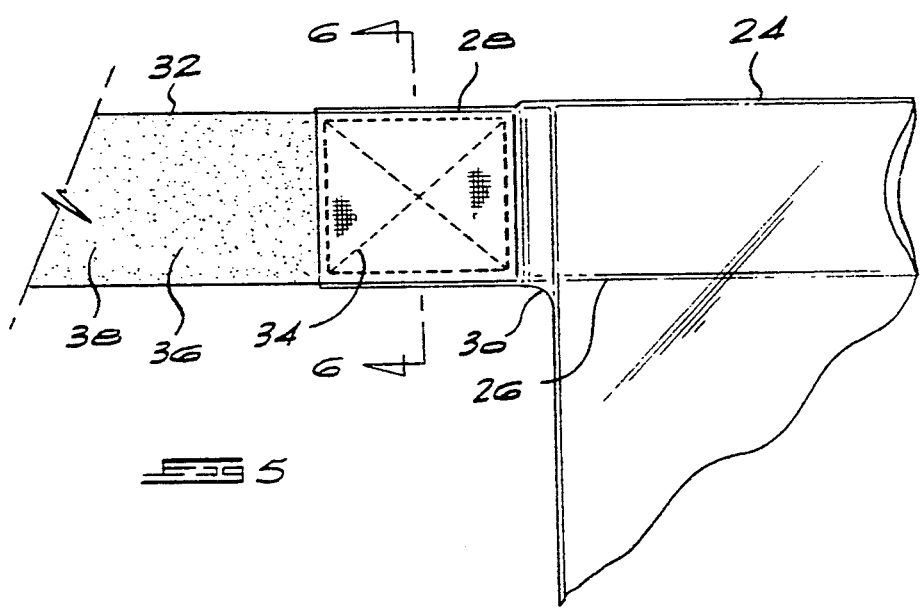

PROTECTIVE SHEATH FOR AN INJURED LIMB

BACKGROUND TO THE INVENTION

This invention relates to a limb sheath for protecting injured limbs.

It often happens that a person who has an injured limb is faced with the problem of keeping the limb dry when bathing or washing parts of the body adjacent to the limb in question. The problem may be especially severe in the case of open burn wounds, plaster casts on broken limbs, and bandaged limbs.

SUMMARY OF THE INVENTION

The invention provides a limb sheath comprising:
a water impervious sleeve made of a first plastics material and having at least one open end through which a limb can be inserted,
a sealing strip which is fastened to and extends about the internal surface of the sleeve at each open end thereof, the sealing strip being made of a second plastics material which is more highly plasticised than the first plastics material, and
an elastic strap which is connected to and extends from the sleeve adjacent each open end thereof, the strap being fastenable to itself by mating components of a self-contact fastener, such components being carried by the strap,
the arrangement being such that with a limb inserted into the sleeve through an open end thereof and with the sealing strip in contact with the limb, the strap can be stretched resiliently, wrapped about the open end and fastened to itself, thereby pressing the sealing strip against the limb to form a water-tight seal at the open end.

The strap may carry the mating components of a VELCRO hook-and-loop fastener on opposite surfaces thereof. In the preferred embodiment, the strap carries one VELCRO hook-and-loop component on one surface thereof and a plurality of spaced apart, mating VELCRO hook-and-loop components on the opposite surface thereof.

Both the first and second plastics materials can be PVC.

In a preferred construction, each strap is connected to a connection tab projecting from the sleeve adjacent the open end thereof. The connection tab can be formed by an extension of the sleeve and an extension of the sealing strip, the connection tab having a thickness made up of four plies of plastic material, two of such plies being of the first plastics material and the other two of such plies being of the second plastics material.

With a view to preventing undue constriction of the limb, the strap should have a width of at least 50 mm.

BRIEF DESCRIPTION OF THE DRAWINGS

The invention will now be described in more detail, by way of example only, with reference to the accompanying drawings in which:

FIG. 4 shows a cross-section at the line 4—4 in FIG. 1;

FIG. 5 illustrates in detail the manner in which the strap is connected to the sleeve of the limb sheath; and FIG. 6 shows an enlarged cross-section at the line 6—6 in FIG. 5.

DESCRIPTION OF EMBODIMENTS

Figure 1:
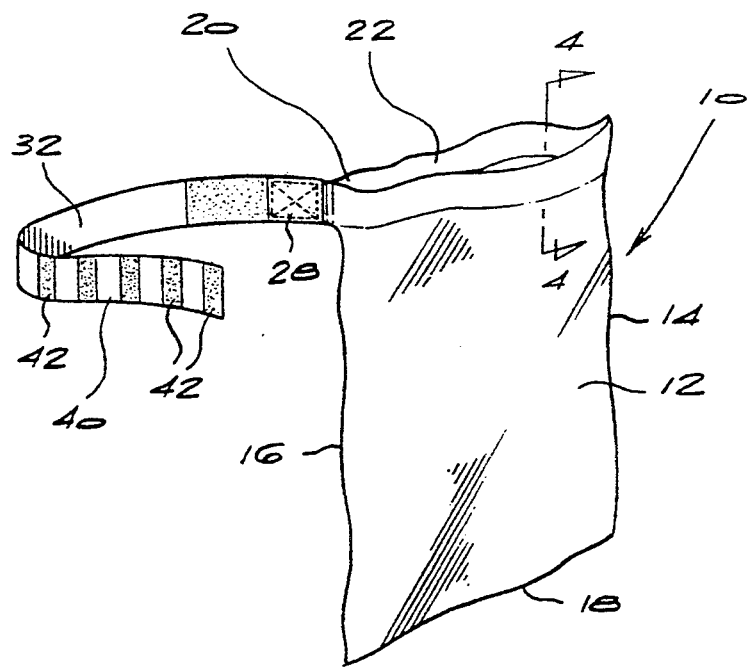
FIG. 1 shows a perspective view of a limb sheath according to the invention.

The illustrated limb sheath 10 has, as its major component, a sleeve 12 of flexible, water-impervious material, in this case PVC (polyvinyl chloride). In a typical case, the PVC of the sleeve 12 has a thickness of the order of 100 $\mu$m. The sleeve 12 in the illustrated case is formed from two sheets of PVC material welded together on the sides 14 and 16 and at the end 18, thereby forming a bag with an open end 20 as illustrated.

In the illustrated case, the length of the sleeve is chosen for it to receive the hand and forearm of an adult. The dimensions of the sleeve may however vary widely from case to case, depending on which limb is to be sheathed and on the size of the person whose limb is to be sheathed. Also, while a specific description is given of a sheath in the form of a bag which has one open end and one closed end, it should be recognised that the invention is also applicable to a sleeve which is open at both ends. For instance, a sleeve with two open ends may be used to protect a bandaged elbow or knee.

Irrespective of whether only one or both ends of the sleeve are open, each open end must be capable of forming a watertight seal against the skin of the wearer once the limb of the wearer has been inserted into the sleeve.

In the illustrated embodiment, there is a sealing strip 22 located at the open end or mouth of the sleeve, on the inner surface thereof. The sealing strip in the illustrated case has a width of 70 mm and a thickness of 250 $\mu$m. It is made of a very soft, highly plasticised PVC.

The term "highly plasticised" may be understood in this specification to mean that the PVC of which the sealing strip is made is more highly plasticised than that of which the sleeve itself is made. In a typical case, the PVC of the sleeve is plasticised to the extent of approximately 20% while the PVC of the sealing strip 22 is plasticised to the extent of approximately 40%. The sealing strip 22 is plasticised to the extent that it has a somewhat "tacky" feel and is capable of forming a good, non-slip seal when placed tightly against human skin.

The sealing strip 22 is welded to the interior surface of the sleeve along lines 24 and 26 (FIG. 5).

At one position around the mouth or open end of the sleeve, the PVC material of which the sleeve is made, and the PVC material of which the sealing strip is made, are extended beyond the periphery of the sleeve to form a connection tab 28, seen in detail in FIGS. 5 and 6.

Bearing in mind that the sleeve itself consists of two sheets of PVC material, and that the extension of the sealing strip 22 will provide a further two layers of PVC material, it will be appreciated that the connection tab has a thickness made up of four superimposed PVC sheets and has a total thickness, in this case, of the order of 700 $\mu$m.

It will be noted from FIG. 5 that the connection tab has a radiused corner 30, and that one end of an elasticised strap 32 is fastened to the connection tab 28 by stitching 34. In the illustrated case, the strap 32 has a relaxed length of approximately 450 mm and a width corresponding to that of the sealing strip and connection tab, i.e. 70 mm.

Sewn to one side 36 of the strap 32 is a length of VELCRO hook-and-loop fastening material 38, in this case a length of male VELCRO hoop-and-loop material. Sewn to the opposite side 40 of the strap 32 are spaced apart patches 42 of mating VELCRO hook-and-loop material, in this case of female type.

Figures 2, 3:
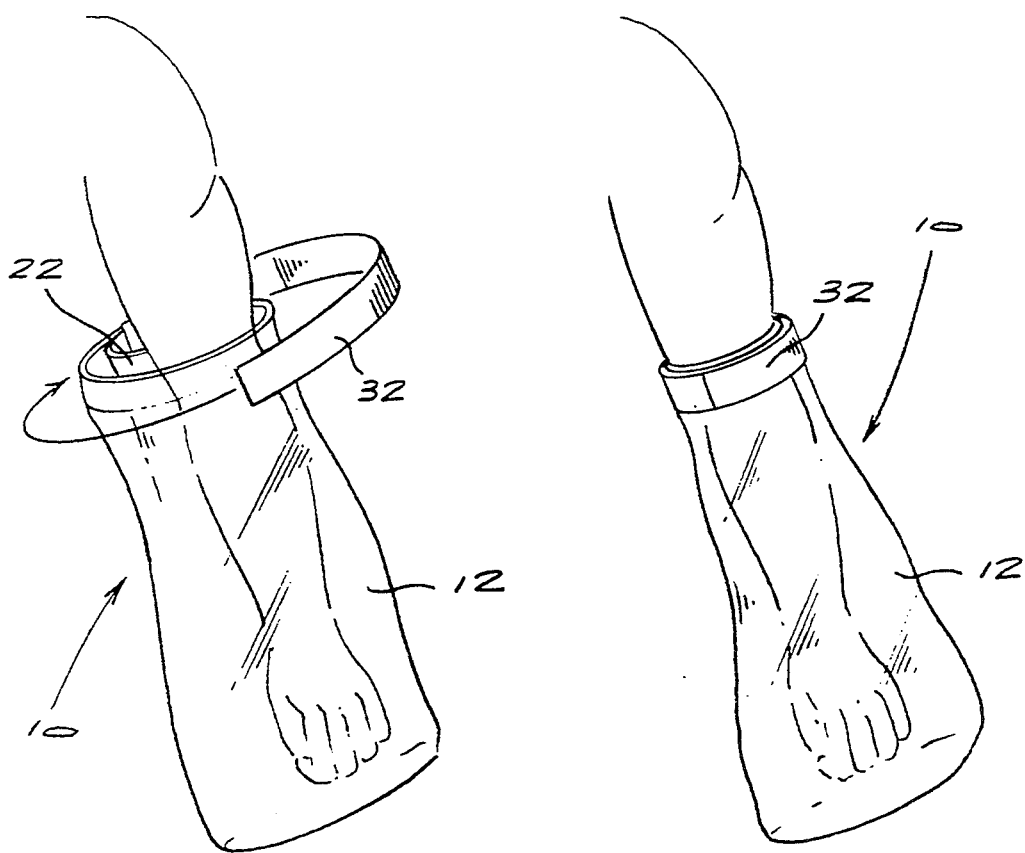
FIG. 2 shows how the limb sheath of FIG. 1 is put on a limb in use.
FIG. 3 shows the limb sheath fastened and sealed in position.

FIGS. 2 and 3 illustrate how the limb sheath 10 is worn. The wearer slips his hand, forearm and elbow into the sleeve 12. Assuming the arm of a normal adult, the sealing strip 22 locates just above the elbow, with the upper arm locating loosely within the sleeve. With his free hand, the wearer then doubles over any excess material at the mouth of the sleeve, and winds the elasticised strap around the upper end of the sleeve, i.e. over the zone in which the sealing strip is in contact with his skin. During this procedure, the strap 32 may be stretched quite considerably, but the wearer should nevertheless not wind the strap so tightly that blood flow is restricted in any way.

The tacky nature of the sealing strip 22 acts to some extent at least to prevent the whole sleeve from rotating on the wearer's arm. Once the winding of the strap has been completed, the wearer brings an appropriate one of the female VELCRO hook-and-loop patches 42 into contact with the male VELCRO hook-and-loop material 38, thereby securing the free end of the strap. In practice, for a given elasticity of the strap 32, the patches 42 are carefully sized and spaced to ensure that appropriate securing contact can be made for a wide range of different upper arm sizes.

Experimentation indicates that the seal formed against the skin by the sealing strip 22 is sufficient to prevent ingress into the sleeve of water during normal bathing or washing procedures. Once the wearer has finished bathing, he forcibly separates the male and female components of the VELCRO hook-and-loop fastener, unwinds the strap 32 and withdraws his forearm and hand from the limb sheath 10 which can be stored for re-use when required again. The PVC of which the sleeve is made has considerable resistance to tearing or puncturing, and it is anticipated that the wearer will be able to re-use the limb sheath many times before it is disposed of.

It will be appreciated that one area of the limb sheath which experiences considerable stress, particularly when the wearer is putting the limb sheath on, is the connection tab 28. It is for this reason that it is considered desirable in the illustrated embodiment to have a connection tab with a considerable thickness as described above, since the more material there is present in the tab, the less is the chance of the tab tearing when stressed as a result of the wearer pulling firmly on the strap 32.

The corner 30, which is in use subjected to a considerable tearing stress, is strengthened by its radiused shape. Added to this there may be extra welding, again for additional strength purposes, in the region of the connection tab 28 and corner 30.

We claim:

1. A limb sheath comprising:
   a water impervious sleeve made of a first plastics material and having at least one open end through which a limb can be inserted,
   a sealing strip which is fastened to and extends about the internal surface of the sleeve at each open end thereof, the sealing strip being made of a second plastics material which is more highly plasticised than the first plastics material,
   a connection tab projecting from the sleeve adjacent the open end thereof, the connection tab being formed by an extension of the sleeve and an extension of the sealing strip, the connection tab having a thickness made up of four plies of plastic material, two of such plies being of the first plastics material and other two of such plies being of the second plastics material, and
   an elastic strap which is stitched to and extends from the connection tab, the strap being fastenable to itself by mating components of a hook-and-loop fastener, such components being carried on opposite surfaces of the strap with one component of the fastener on one surface of the strap and a plurality of mating components in spaced apart relationship on the opposite surface of the strap,
   the arrangement being such that with a limb inserted into the sleeve through an open end thereof and with the sealing strip in contact with the limb, the strap can be stretched resiliently, wrapped about the open end and fastened to itself, thereby pressing the sealing strip against the limb to form a water-tight seal at the open end.

2. A limb sheath according to claim 1 wherein the first and second plastics materials are both polyvinyl choride.

3. A limb sheath according to claim 2 wherein the first plastics material has a thickness of the order of 100 $\mu$m.

4. A limb sheath according to claim 3 wherein the second plastics material has a thickness of the order of 250 $\mu$m.

5. A limb sheath according to claim 1 wherein the strap has a width the same as that of the sealing strip.

6. A limb sheath according to claim 5 wherein the strap has a width of at least 50 mm.

* * * * *

UNITED STATES PATENT AND TRADEMARK OFFICE
CERTIFICATE OF CORRECTION

PATENT NO. : 5,395,302
DATED : March 7, 1995
INVENTOR(S) : Botha, et al

It is certified that error appears in the above-indentified patent and that said Letters Patent is hereby corrected as shown below:

Column 4, line 41, Claim 2, "choride" should be --chloride--.

Signed and Sealed this

Thirteenth Day of June, 1995

Attest:

BRUCE LEHMAN

Attesting Officer       Commissioner of Patents and Trademarks